(12) United States Patent
Smith et al.

(10) Patent No.: US 12,174,202 B2
(45) Date of Patent: Dec. 24, 2024

(54) SYSTEMS AND METHODS FOR ELECTROCHEMICAL POINT-OF-CARE DETECTION OF HEMOGLOBIN

(71) Applicant: POLYMER TECHNOLOGY SYSTEMS, INC., Whitestown, IN (US)

(72) Inventors: Donnie Smith, Indianapolis, IN (US); Brittney L Werner, Fairland, IN (US); Gary L. Hughes, Camby, IN (US); Jie Chen, Whitestown, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 0 days.

(21) Appl. No.: 18/328,942

(22) Filed: Jun. 5, 2023

(65) Prior Publication Data
US 2023/0305026 A1    Sep. 28, 2023

Related U.S. Application Data

(62) Division of application No. 16/698,872, filed on Nov. 27, 2019, now Pat. No. 11,693,016.

(Continued)

(51) Int. Cl.
*G01N 33/72* (2006.01)
*C12N 9/50* (2006.01)
*G01N 27/327* (2006.01)

(52) U.S. Cl.
CPC ............. *G01N 33/721* (2013.01); *C12N 9/50* (2013.01); *G01N 27/3272* (2013.01); *G01N 33/723* (2013.01); *G01N 33/726* (2013.01)

(58) Field of Classification Search
CPC .......... C07K 14/805; C12N 9/50; C12Q 1/26; G01N 27/3272; G01N 33/49; G01N 33/721; G01N 33/723; G01N 33/726

(Continued)

(56) References Cited

U.S. PATENT DOCUMENTS

| 4,876,205 A | 10/1989 | Green et al. |
| 7,005,273 B2 * | 2/2006 | Heller ............... F02B 75/20 |
| | | 436/66 |

(Continued)

FOREIGN PATENT DOCUMENTS

| EP | 1889918 | * | 2/2008 |
| EP | 3020825 A1 | | 5/2016 |

OTHER PUBLICATIONS

Nanjo et al. Analytical Chimica Acta, vol. 583, pp. 45-54, Sep. 26, 2006.*

(Continued)

*Primary Examiner* — Maureen Wallenhorst
(74) *Attorney, Agent, or Firm* — Haynes and Boone, LLP

(57) ABSTRACT

A method includes lysing the red blood cells of a whole blood sample, oxidizing the free hemoglobin in the lysed sample, and cleaving FVH from the hemoglobin A1C to form an electrochemical test solution. A first portion of the electrochemical test solution is reacted with fructosyl peptide oxidase and a reduced ruthenium mediator to form a first reaction product. A first electrical property of the first reaction product is measured, the measurement being indicative of hemoglobin A1C in the blood sample. A second portion of the electrochemical test solution is reacted with ferrocyanide to form a second reaction product. A second electrical property of the second reaction product is measured, the measurement being indicative of total hemoglobin in the blood sample. Hemoglobin A1C, total hemoglobin, and % HbA1C are determined based on the first and second electrical properties. Also provided are systems and components useful in performing the disclosed methods.

5 Claims, 4 Drawing Sheets

Related U.S. Application Data

(60) Provisional application No. 62/772,789, filed on Nov. 29, 2018.

(58) Field of Classification Search
USPC ........... 436/63, 66, 67, 149, 150; 422/82.01, 422/82.02; 435/23, 25
See application file for complete search history.

(56) References Cited

U.S. PATENT DOCUMENTS

| | | | |
|---|---|---|---|
| 7,005,276 B1 | 2/2006 | Flegel et al. | |
| 8,673,646 B2 | 3/2014 | Yuan | |
| 11,199,551 B1* | 12/2021 | Connolly | ......... A61B 5/150358 |
| 11,693,016 B2* | 7/2023 | Smith | ................. C07K 14/805 |
| | | | 436/66 |
| 2010/0025264 A1 | 2/2010 | Yuan et al. | |
| 2010/0089774 A1 | 4/2010 | Manohar et al. | |
| 2012/0202235 A1* | 8/2012 | Ikebukuro | ............ G01N 33/723 |
| | | | 435/23 |
| 2012/0305395 A1 | 12/2012 | Heller | |
| 2013/0078664 A1* | 3/2013 | Yuan | .................... G01N 33/723 |
| | | | 435/28 |
| 2013/0115646 A1* | 5/2013 | Soya | ........................ C12Q 1/54 |
| | | | 435/23 |
| 2013/0171676 A1* | 7/2013 | Murakami | ............... C12Q 1/26 |
| | | | 435/23 |
| 2016/0123999 A1 | 5/2016 | Ogawa et al. | |
| 2016/0355862 A1 | 12/2016 | Deng et al. | |
| 2018/0251811 A1 | 9/2018 | Hughes et al. | |
| 2019/0041406 A1* | 2/2019 | Hughes | ................ A61B 5/1486 |

OTHER PUBLICATIONS

Extended European Search Report dated Sep. 20, 2022 issued in related European patent application No. 19889012.1 (8 pages).

Q.H. Gibson, "The Reduction of Methaemoglobin by Ascorbic Acid," Biochem J. 1943; 37(5): 615-8 (4 pages).

International Search Report and Written Opinion dated Apr. 6, 2020 issued in related PCT App. No. PCT/US19/63789 (17 pages).

* cited by examiner

SYSTEMS AND METHODS FOR ELECTROCHEMICAL POINT-OF-CARE DETECTION OF HEMOGLOBIN

CROSS REFERENCE

This application is a divisional application of U.S. patent application Ser. No. 16/698,872 filed Nov. 27, 2019 now U.S. Pat. No. 11,693,016, and claims the benefit of U.S. provisional application No. 62/772,789, filed Nov. 29, 2018, the entirety of which is hereby incorporated by reference.

BACKGROUND

Glycation of hemoglobin occurs primarily at the amino termini of beta chains, as well as other sites with free amino groups. The most prevalent and well-characterized species of glycated hemoglobin A is A1C, making up approximately 3% to 6% of the total hemoglobin in healthy individuals. Hemoglobin A undergoes a slow glycation with glucose that is dependent on the time-average concentration of glucose over the 120-day life span of red blood cells. Hemoglobin A1C ("HbA1C") is a type of glycated hemoglobin which is formed when glucose binds to the N-terminal valine residue of the β-chains of hemoglobin. The correlation of A1C and blood glucose levels make it a useful method for monitoring long-term blood glucose levels in people with diabetes. The mean (average) blood glucose level is a function of the A1C levels and is therefore derivable.

% HbA1C is the ratio of glycated A1C hemoglobin to total hemoglobin expressed as a percentage. % HbA1C is an indicator of how well or how poorly diabetics have controlled their diabetes, and it can also be an indicator of pre-diabetes. % HbA1C is therefore an important diagnostic tool for the diagnosis and treatment of diabetes. The amount of glycated hemoglobin in the blood as a part of total hemoglobin is a good indicator of how well the body has managed glucose levels.

Point of Care ("POC") and home testing for A1C and ultimately % HbA1C are desirable for both patient and doctor. High levels of blood glucose cause over-glycation of proteins, including hemoglobin, throughout the body. Regular measurement of HbA1C allows doctors to help their patients better manage the disease by providing them with the information to alter their medications, or by suggesting lifestyle changes.

Thus, A1C and % HbA1C measurements are an important indicator in the monitoring and diagnosis of diabetes mellitus. The ability to quickly and accurately determine A1C and total hemoglobin, particularly in a POC system, is therefore of great importance. However, some measurement methods are unable to provide accurate results across the many hemoglobin variants found naturally in patients. An electrochemical test combining determination of both HbA1c and total hemoglobin would be independent of hemoglobin variants and could determine hemoglobin parameters with a single blood sample. This would represent a significant step forward in the health care of diabetics.

SUMMARY

In one aspect there is provided a method for electrochemically detecting free hemoglobin in a sample solution. The free hemoglobin is oxidized to $Fe^{+3}$ and fructosyl-valine-histidine ("FVH") is cleaved, resulting in an electrochemical test solution comprising a mixture of hemoglobin, FVH, and hemoglobin degradation products. A first portion of the electrochemical test solution is combined with a chemistry including fructosyl peptide oxidase ("FPOX") and a reduced ruthenium mediator to form a first reaction product. A first electrical property of the first reaction product is measured, this measurement being indicative of the amount of hemoglobin A1C in the sample solution. A second portion of the electrochemical test solution is combined with a chemistry including ferrocyanide (potassium hexacyanoferrate $Fe^{+2}$) to form a second reaction product. A second electrical property of the second reaction product is measured, this measurement being indicative of the amount of total hemoglobin in the sample solution. The A1C and total hemoglobin determinations are combined to derive % HbA1C. Systems and components useful in the disclosed methods are also provided.

In another aspect, an electrochemical test system for determining hemoglobin A1C and % HbA1C is disclosed. The test system includes a sampler and first and second test strips configured to facilitate the determination of A1C and total hemoglobin. The sampler includes a pre-analytical solution comprising components for lysing red blood cells, oxidizing free hemoglobin to $Fe^{+3}$, and cleaving FVH from free hemoglobin. The first test strip includes a reaction chemistry comprising FPOX and a reduced ruthenium mediator. The second test strip includes a reaction chemistry comprising FPOX and ferrocyanide.

In one aspect, fast, reliable and accurate quantitation of hemoglobin A1C and total hemoglobin in a whole blood sample is achieved. In another aspect, quantitation of % HbA1C is accomplished as part of an overall electrochemical measurement system.

In a further aspect, methods and systems are provided for measuring hemoglobin A1C and total hemoglobin in portions of a single electrochemical test solution prepared from a whole blood sample.

As a further aspect, because the measurements are both electrochemical, they do not have a specificity for hemoglobin variants, so different variants do not impact the results.

In one embodiment, a method for electrochemically detecting free hemoglobin in a sample solution includes oxidizing the free hemoglobin and cleaving fructosyl-valine-histidine (FVH) from the free hemoglobin to form an electrochemical test solution including a mixture of hemoglobin, FVH, and hemoglobin degradation products. The method further includes reacting a first portion of the electrochemical test solution with a chemistry including fructosyl peptide oxidase and a reduced ruthenium mediator to form a first reaction product. The method further includes measuring a first electrical property of the first reaction product which is indicative of the amount of hemoglobin A1C in the sample solution. The method further includes reacting a second portion of the mixture with a chemistry including fructosyl peptide oxidase and ferrocyanide to form a second reaction product. The method further includes measuring a second electrical property of the second reaction product which is indicative of the amount of total hemoglobin in the sample solution. The method further includes determining the amounts of hemoglobin A1C and of total hemoglobin of the sample solution based on the measured first and second electrical properties, respectively. Alternatively, the method further includes determining the % HbA1C based on the determined amounts of hemoglobin A1C and total hemoglobin. In one alternative, the first electrical property is a current produced in response to a voltage applied to the first reaction product and the method includes applying a voltage to the first reaction product, detecting a first resulting current, and determining the amount of hemoglobin A1C based on the first resulting current. In another alternative, the second electrical property is a current produced in response to a voltage applied to the second reaction product and the method includes applying a voltage to the second reaction product, detecting a second resulting current, and determining the amount of total hemoglobin based on the second resulting current. Alternatively, the first electrical property is a current produced in response to a voltage applied to the first reaction product and the method includes applying a voltage to the first reaction product, detecting a first resulting current, and determining the amount of hemoglobin A1C based on the first resulting current. In another alternative, the applied voltage is a negative voltage. Alternatively, the applied voltage is a negative voltage of 525 mV. In one alternative, the oxidizing includes combining an oxidizing agent with the free hemoglobin. Alternatively, cleaving includes combining the oxidized free hemoglobin with Neutral Enzyme Proteinase. In another alternative, the oxidizing includes combining an oxidizing agent with the free hemoglobin. Alternatively, the sample solution is a whole blood sample containing red blood cells and the method further includes prior to the oxidizing and cleaving steps, lysing the red blood cells to form a lysed sample solution containing the free hemoglobin. In another alternative, oxidizing includes combining an oxidizing agent with the free hemoglobin. Alternatively, the cleaving includes combining the oxidized free hemoglobin with Neutral Enzyme Proteinase. Alternatively, oxidizing includes combining an oxidizing agent with the free hemoglobin. In another alternative, the mixing the lysed sample solution with a pre-analytical solution containing components for performing the steps of lysing, oxidizing and cleaving.

In one embodiment, a system for the determination of A1C and total hemoglobin includes a sampler including a pre-analytical solution including components for lysing red blood cells, oxidizing free hemoglobin to $Fe^{+3}$, and cleaving FVH from free hemoglobin to form an electrochemical test solution. The system further includes a first test strip including a reaction chemistry including fructosyl peptide oxidase and a reduced ruthenium mediator for the electrochemical determination of A1C. The system further includes second test strip including a reaction chemistry including fructosyl peptide oxidase and ferrocyanide for the electrochemical determination of total hemoglobin. Alternatively, the pre-analytical solution includes a Neutral Enzyme Proteinase. In one alternative, the pre-analytical solution includes Zwittergent 3-14™(n-Tetradecyl-N,N-dimethyl-3-ammonio-1-propanesulfonate). In another alternative, the pre-analytical solution includes:
- 1.5% Triton X-100™(t-Octylphenoxypolyethoxyethanol, Polyethylene glycol tert-octylphenyl ether);
- 880 mM Imidazole;
- 10 mM NaCl;
- 3 mM CaCl2);
- 47.6 mM Tetradecyltrimethylammonium bromide (TTAB);
- 8.1 mM 1,2-benzoisothiazol-3-one sodium salt (Isothiazoline); and
- 35 kU/mL NEP-801.

Alternatively, the pre-analytical solution is configured to be combined with a sample and applied to both the first and second test strip to achieve an analytical result.

DESCRIPTION

Figure 1:
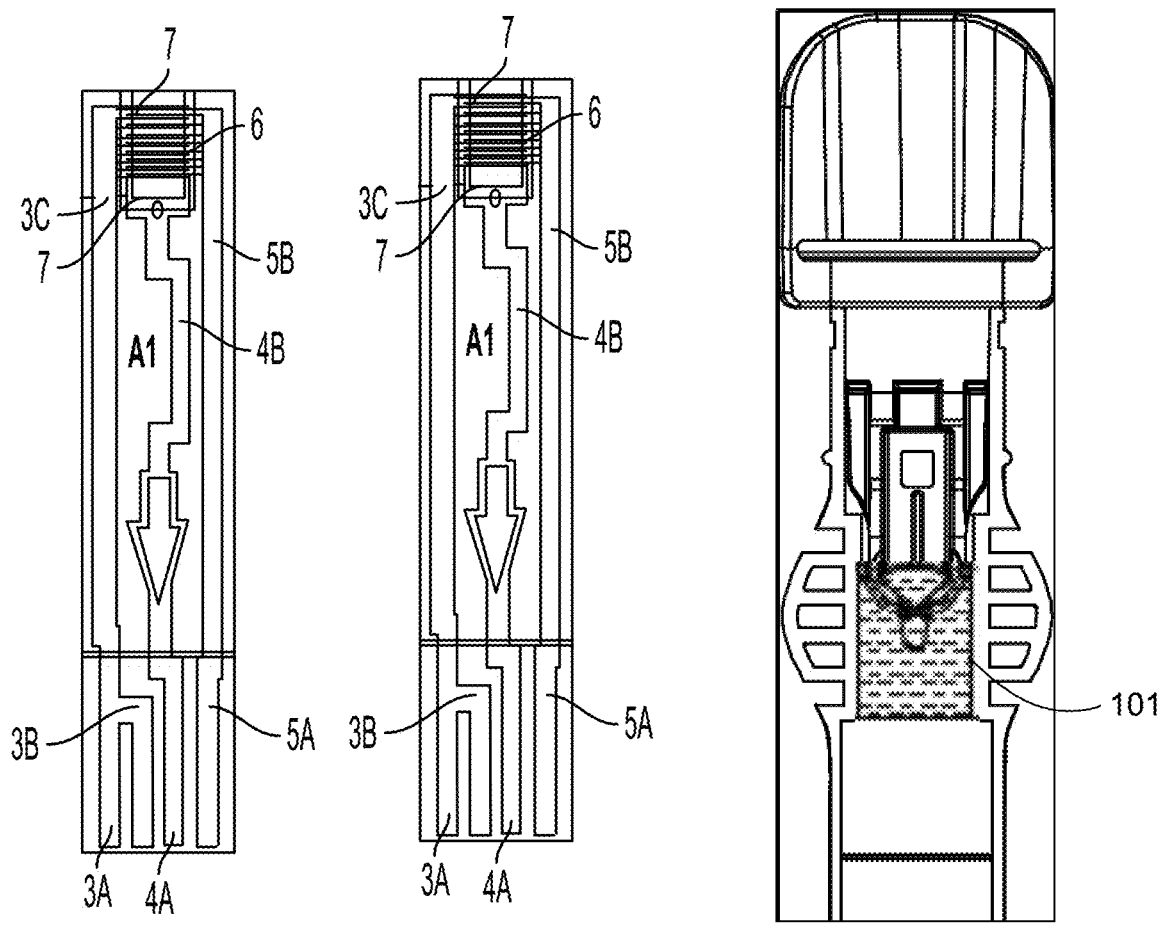
FIG. 1 shows one embodiment of electrochemical test strips and a sampler for use in determining hemoglobin A1C, total hemoglobin, and % HbA1C.

Certain terminology is used herein for convenience only and is not to be taken as a limitation on the embodiments of the methods and systems for electrochemical detection and quantification of hemoglobin A1C, total hemoglobin, and % HbA1C. The preparation, detection and quantification techniques described herein enable quick and accurate electrochemical detection of % HbA1c.

Of particular note is the fact that the disclosed methods and systems for detecting blood hemoglobin may be used in a portable, low cost, point-of-care (POC) device. The testing requires only a fingerstick of blood, rather than a venous draw, and the testing may therefore be performed by self-testing at home.

Pre-Analytical Solution Preparation

The methods and systems are based on the preparation of an electrochemical test solution suitable prepared from a whole blood sample and suitable for electrochemical determination of both A1C and total hemoglobin. This electrochemical test solution comprises oxidized free hemoglobin from which FVH has been cleaved. In one aspect, the initial preparation includes the following steps performed on a solution containing free hemoglobin:
- oxidation of free hemoglobin in a blood sample, and
- cleavage of FVH from the free hemoglobin.

This yields an electrochemical test solution comprising hemoglobin, FVH, and hemoglobin degradation products. The oxidation and cleavage steps may be preceded by steps including obtaining a whole blood sample and lysing the red blood cells to provide the free hemoglobin solution.

Preparation of the electrochemical test solution may be accomplished by mixing the whole blood sample with a pre-analytical solution which includes components for one or more of the lysing, oxidizing and cleaving steps. The pre-analytical solution may also function to dilute the test sample to a concentration appropriate for use in the analysis. In one aspect, the blood sample is mixed with the pre-analytical solution in a suitable ratio, such as a 1:5 ratio. Additional components also may be included in the pre-analytical solution to provide other functions such as buffering, preservation and stabilization.

It has been found that hemoglobin A1C and total hemoglobin may be determined from as little as a single drop of blood. However, in alternative embodiments the determination of hemoglobin utilizes either capillary or venous blood samples in volumes such as 10 μL to 100 μL, which may be drawn into Li-heparin or EDTA tubes.

There is a difference between capillary and venous blood. Capillary blood typically reports higher levels of hemoglobin than venous blood. However, this difference is readily addressed by the use of different calibration curves based on the type of sample.

Lysing Agents

In most embodiments, including in the use of a POC system, the first step in performing the assay is to lyse the red blood cells to release the hemoglobin. Lysing agents are well known in the art and include, for example, Triton X-100™(t-Octylphenoxypolyethoxyethanol, Polyethylene glycol tert-octylphenyl ether) and other suitable surfactants. Many such surfactants are available, with some surfactants being more efficient at lysing red blood cells. The surfactant may, for example, be non-ionic, anionic, cationic, or zwitterionic. In one embodiment, a zwitterionic surfactant is used as it keeps the slightly denatured hemoglobin in solution. Zwittergent 3-14™(n-Tetradecyl-N,N-dimethyl-3-ammonio-1-propanesulfonate) appears to keep the hemoglobin from falling out of solution, making it unable to react with the protease. This is an important characteristic of the surfactant.

Oxidation of the Free Hemoglobin

The pre-analytical solution further includes one or more components to oxidize the hemoglobin. Oxidation of the hemoglobin is an important aspect of the assay. This allows cleavage of Fructosyl-Valine-Histidine (FVH) from the hemoglobin by the protease. Oxidation also removes interference which would other result from the presence of reduced hemoglobin. That is, if the hemoglobin is not oxidized prior to coming into contact with the mediator, it will be oxidized by the mediator, creating an electrochemical response and unwanted background. Unfortunately, many of the common substances that form methemoglobin are also electrochemically active. Thus, an oxidizing agent is used that oxidizes a high percentage of the heme iron of the hemoglobin to $Fe^{+3}$, does not react electrochemically in the test system, and does not interfere with the protease or the fructosyl peptide oxidase.

Various oxidizing agents are known and may be evaluated for use herein. These agents may oxidize the hemoglobin or may facilitate oxidation in combination with one or more other oxidizing agents. However, not all oxidizing agents are useful in the disclosed electrochemical hemoglobin method.

In one embodiment, TTAB and an isothiazoline derivative are used in combination, providing surprisingly superior results as compared to the use of either agent alone. In an embodiment, 1-Dodecyl pyridinium chloride is used as the cationic surfactant, and 1,2 Benzisothiazol-3(2H)-one is used as the isothiazoline derivative.

Cleavage of FVH

The pre-analytical solution further includes a protease, such as Neutral Enzyme Proteinase (NEP) to cleave the FVH. The protease degrades the glycated hemoglobin selectively to a glycated hemoglobin degradation product. The resulting solution containing the FVH is tested electrochemically for determining glycated hemoglobin.

In order to optimize the digestion of the protease, the hemoglobin is placed in a relaxed state and is therefore able to unfold and spread out. Commercial A1C assays for hospital analyzers have large dilution factors (e.g. 1 part blood to 100 parts reagent). However, in an electrochemical POC assay, the sample cannot be diluted so much as to not have enough signal to read. It is therefore important for a POC system that the protease work efficiently. In some embodiments, imidazole may be used as a hemoglobin ligand. Imidazole ($C_3H_4N_2$) binds to the hemoglobin and thereby causes it to be in a relaxed state, allowing the protease to react more efficiently.

In various alternatives, other analogs of imidazole may be used. Analogs may include Benzimidazole, Dihydroimidazole, Pyrrole, Oxazole, Thiazole, Pyrazole, Triazoles, Tetrazole, Pentazole, Furazan, Isothiazole, Thiazole, Thiadiazole, and various other Azoles. Additionally, histidine or other molecules having imidazole or an imidazole analog as a side chain may enhance the protease. Other hemoglobin binding ligands such as sodium azide and pyridine have been found to not have the same effect as imidazole.

Pre-Analytical Solution

By way of example, a suitable pre-analytical solution, adjusted to a pH of 7.5, can be made with the following components:
  1.5% Triton X-100™(t-Octylphenoxypolyethoxyethanol, Polyethylene glycol tert-octylphenyl ether);
  880 mM Imidazole;
  10 mM NaCl;
  3 mM CaCl2);
  47.6 mM Tetradecyltrimethylammonium bromide (TTAB);
  8.1 mM 1,2-benzoisothiazol-3-one sodium salt (Isothiazoline); and
  35 kU/mL NEP-801.

Glycated Hemoglobin

Determination of glycated hemoglobin A1C from the oxidized and cleaved, electrochemical test solution is accomplished by an electrochemical method. The method involves the following steps:
  reacting a first portion of the mixture with FPOX and a reduced ruthenium mediator to form a first reaction product;
  measuring an electrical property of the first reaction product which is proportional to the amount of glycated A1C hemoglobin in the sample; and
  determining the amount of A1C in the blood sample from the electrical measurement.

In one aspect, the electrochemical test solution containing FVH is dosed onto a test strip containing the FPOX and ruthenium hexamine trichloride ($RuIII(NH_3)_6Cl_3$) mediator. By way of example, the test strip is coated with a 100 mM solution of electrochemical test reagent including FPOX, the ruthenium mediator, and the following additional components:
  Polymer—Polyethylene Oxide or Polyvinylacetate;
  Surfactant—Triton-X-100™(t-Octylphenoxypolyethoxyethanol, Polyethylene glycol tert-octylphenyl ether); and
  Buffer—N-tris(Hydroxymethyl)methyl-4-aminobutanesulfonic acid (TABS) 100 mM.
The resulting reaction generates electrons which produce a current that is proportional to the FVH in the sample.

Total Hemoglobin

In another aspect, the methods and systems include the determination of total hemoglobin from a second portion of the oxidized electrochemical test solution. With the heme iron as $Fe^{+3}$, it has been determined that a reaction with ferrocyanide allows for measurement of the reduction of the hemoglobin as an accurate indicator of total hemoglobin.

In a particular aspect, the second portion of the electrochemical test solution is reacted with a test reagent comprising ferrocyanide (potassium hexacyanoferrate $Fe^{+2}$) to form a second reaction product. FPOX is not needed for the total hemoglobin reaction. A second electrical property of the second reaction product is measured which is proportional to the amount of total hemoglobin in the blood sample. Further, the electrochemical determinations of both A1C and total hemoglobin are used to derive the % HbA1C for the blood sample.

The electrochemical test solution is dosed onto a test strip containing the FPOX and ferrocyanide mediator. By way of example, the test strip is coated with a 100 mM solution of electrochemical test reagent including FPOX, the ferrocyanide mediator, and the following components:
  Polymer—Polyethylene Oxide or Polyvinylacetate;
  Surfactant—Triton-X-100™(t-Octylphenoxypolyethoxyethanol, Polyethylene glycol tert-octylphenyl ether); and
  Buffer—N-tris(Hydroxymethyl)methyl-4-aminobutanesulfonic acid (TABS) 100 mM.

The electrochemical test solution is dosed onto the test strip. Following a 10 second rest time, a negative current of −525 mV is applied for a suitable period of time, e.g., twenty seconds. This reaction generates electrons which produce a current that is proportional to the total hemoglobin in the sample. The steady state current is proportional to the amount of hemoglobin in the sample.

Figure 2:
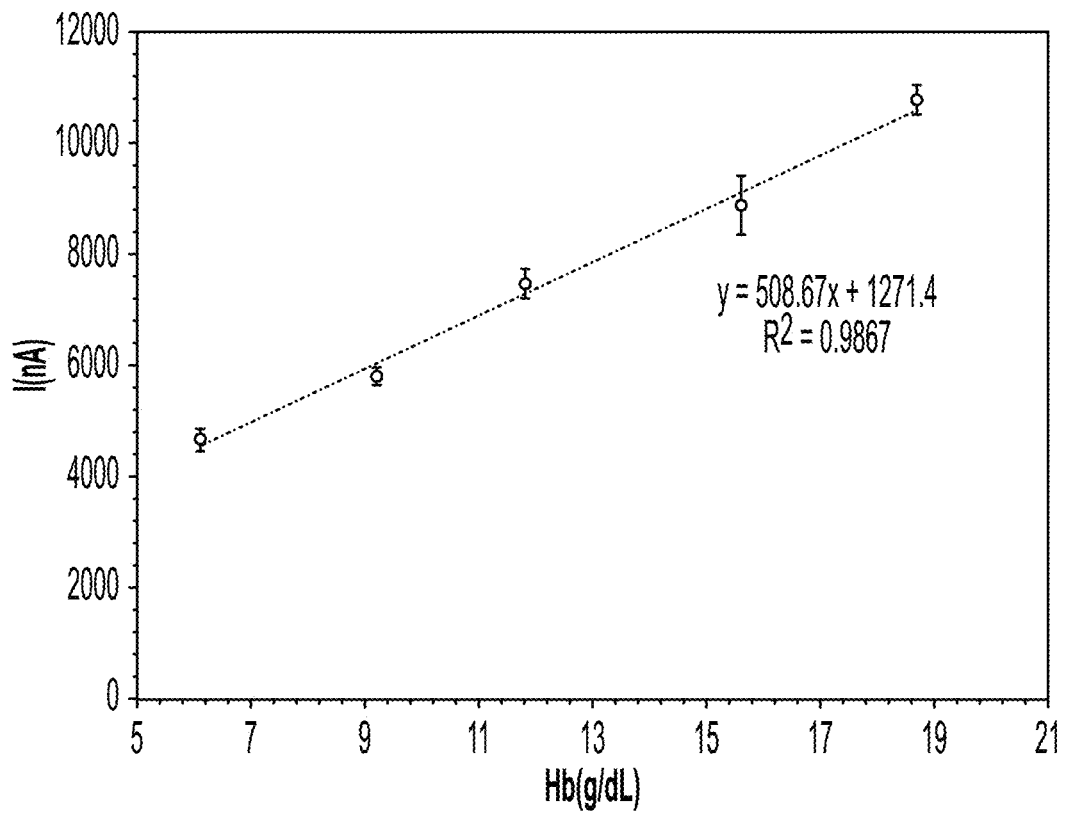
FIG. 2 shows experimental results for a cyclic voltammetry curve of current versus potential for embodiments of the test strips and chemistries described.

Reacting FPOX/ferrocyanide with the oxidized electrochemical test solution resulted in the cyclic voltammetry curve of current versus potential, showing a peak around −450 mV shown in FIG. 2.

Test Strip Design

The foregoing reactions suitably, but not necessarily, take place on test strips. The test strips may have a variety of designs, and may be selected, for example, from a number of test strips known in the art to be useful for electrochemical tests of this general type.

In a basic design, the test strips include a non-conductive base layer with a conductive layer deposited on top which is ablated to make an electrode pattern. The electrode pattern may include, for example, a working electrode, a counter electrode, and one or more fill detect electrodes. The electrode material can be platinum, palladium, carbon, gold, or other suitable materials, with gold being preferred. A spacer is laid over the electrode pattern and a roof is placed on top of the spacer, thereby defining a capillary passageway from a dose port to a reaction chamber. The roof contains a hole to vent air as the test solution flows into the reaction space by capillary action.

Referring to FIG. 1, the test strips are shown as having a working electrode, counter electrode, and a fill detect electrode as well as sampler 101. Each strip is made with gold coated on a polyethylene surface. The size, shape and spacing of the working and counter electrodes is not critical and may be determined by those skilled in the art without undue experimentation. The electrodes may be interdigitated to increase signal response. In one embodiment, the electrode elements have a spacing of 38 µm to 100 µm. Smaller spacings may further increase the signal observed. In FIG. 1, electrode lead 3A includes a loop portion 3B, that allows the insertion of the test strip to be detected by the meter using a u-shaped circuit. The upper portion, interconnector 3C, interconnects to one half of the electrodes of electrodes 6. The upper portion, interconnector 5B, interconnects to the other half of the electrodes of electrodes 6, so that one half of the electrodes may function as an electrode and the other half a counter electrode. Additionally, a reference electrode interconnector 4B may be included as is typical. Dielectrics 7, as shown, surround the test area and serve to prevent current or voltage leakage during testing. Typically, dielectrics 7 comprise, glass, sitall, or other insulting ceramic.

Each test strip is prepared to include the electrochemical test reagent containing the FPOX and mediator in the reaction chamber. The electrochemical test reagent has a suitable pH as known in the art, such as 10.5, and may further include other components, such as the following:
  DI Water
  Polyethylene Oxide (1%)
  Triton-X 100™(t-Octylphenoxypolyethoxyethanol. Polyethylene glycol tert-octylphenyl ether) (0.1%)
  TABS Buffer (20 mM)

The test strip reagent is formulated and then applied to the test strip and allowed to dry. The test strips have disparate mediators, one with reduced ruthenium mediator and the other ferrocyanide.

Calibration Curves

The electrochemical reaction schemes disclosed herein are suitable for use in conventional fashion with calibration curves. A calibration curve may be developed which correlates the response signal to a concentration of A1C or total hemoglobin. As known in the art, a series of tests are conducted at varying concentrations of A1C and total hemoglobin in order to establish a correlation to signal response for the desired range of concentrations. The results provide calibration curves for the electrochemical tests correlating, for example, the electrochemical signal in nanoamps (nA) with the concentration of hemoglobin in millimolar (mM) units. In the alternative, an algorithm, look-up table, or the like may instead or in addition be derived which similarly correlates the response signal to concentration.

EXAMPLES

Experiments have been performed showing the excellent determination of A1C and total hemoglobin using the disclosed electrochemical methods and systems.

Example 1—Pre-Analytical Solution

In an exemplary embodiment, the pre-analytical solution, adjusted to a pH of 7.5, was made with the following components:
  1.5% Triton X-100™(t-Octylphenoxypolyethoxyethanol, Polyethylene glycol tert-octylphenyl ether);
  880 mM Imidazole;
  10 mM NaCl;
  3 mM CaCl2);
  47.6 mM Tetradecyltrimethylammonium bromide (TTAB);
  8.1 mM 1,2-benzoisothiazol-3-one sodium salt (Isothiazoline) and
  35 kU/mL NEP-801.

Example 2-Test Strip

A test strip was prepared having interdigitated working and counter electrodes. A third electrode was provided for fill detection. The electrode material was gold and was coated on a polyethylene base film. The electrodes were produced by laser ablation. A spacer defined the reagent chamber and a roof with vent hole functioned as a lid.

Each strip was coated with a 100 mM solution of the electrochemical test reagent. For total hemoglobin, for example, ferrocyanide buffered to 6.5 to 11 pH was used.

Polyvinylacetate was used to help reagent setup. Triton-X 100™ t-Octylphenoxypolyethoxyethanol. Polyethylene glycol tert-octylphenyl ether) was added to help spread the reagent over the electrode area. In one embodiment, the reactants were combined with the following components and had a pH of 9.5:

Polymer—Polyethylene Oxide or Polyvinylacetate;
Surfactant—Triton-X-100™(t-Octylphenoxypolyethoxyethanol, Polyethylene glycol tert-octylphenyl ether); and
Buffer—N-tris(Hydroxymethyl)methyl-4-aminobutanesulfonic acid (TABS) 100 mM.

The total mixture was applied to at least the working electrode and allowed to dry.

Example 3—Total Hemoglobin

Blood was taken from 1 or more donors and hematocrit was adjusted, usually within a range of 20-60%. Blood was mixed with the pre-analytical solution at a 1:5 ratio, usually using 25 uL of blood to 125 uL of pre-analytical solution. This mixture was then heated at 37° C. for 5 minutes. As described herein, the combining of the blood sample with the pre-analytical solution resulted in lysing of the red blood cells, oxidation of reduced hemoglobin iron to $Fe^{+3}$, and cleaving of the FVH.

Figure 3:
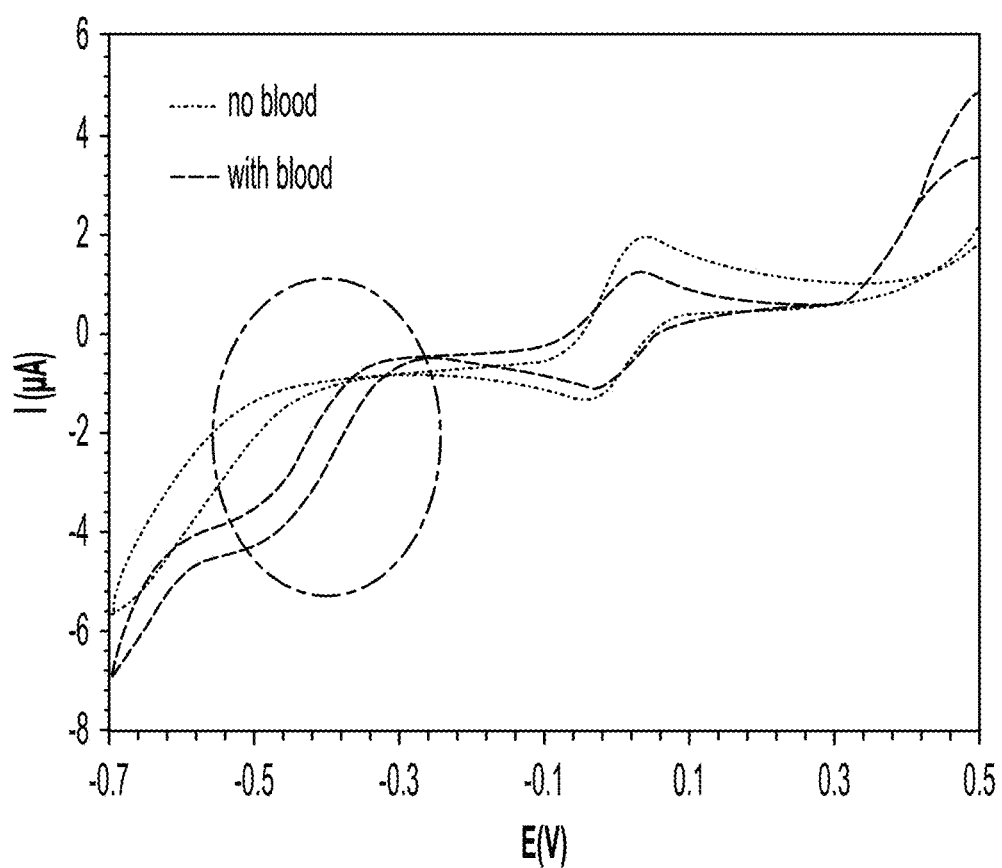
FIG. 3 shows testing results for an embodiment of an electrochemical test strip for use in determining hemoglobin A1C, total hemoglobin, and % HbA1C.

A test strip prepared in accordance with Example 2 and containing ferrocyanide as the mediator was dosed with the heated electrochemical test solution. Detection of a dose at the dose detect electrode was followed by a hold time of 10 seconds. A negative potential of −525 mV was then applied for twenty seconds. The measured current at 10 seconds of measurement (20 seconds after dose detection) was proportionate to the amount of total hemoglobin in the sample as shown in FIG. 3.

Plotting the current measured against time gave a decay that reached a steady state, usually 5-10 seconds after the start of the reaction. The current at 10 seconds was indicative of the amount of hemoglobin in the sample. Smoothing techniques such as rolling averages may be used to increase precision of the measurement. Total hemoglobin was determined using a Hemocue Hb 201+ as a reference method.

Example 5

Figure 4:
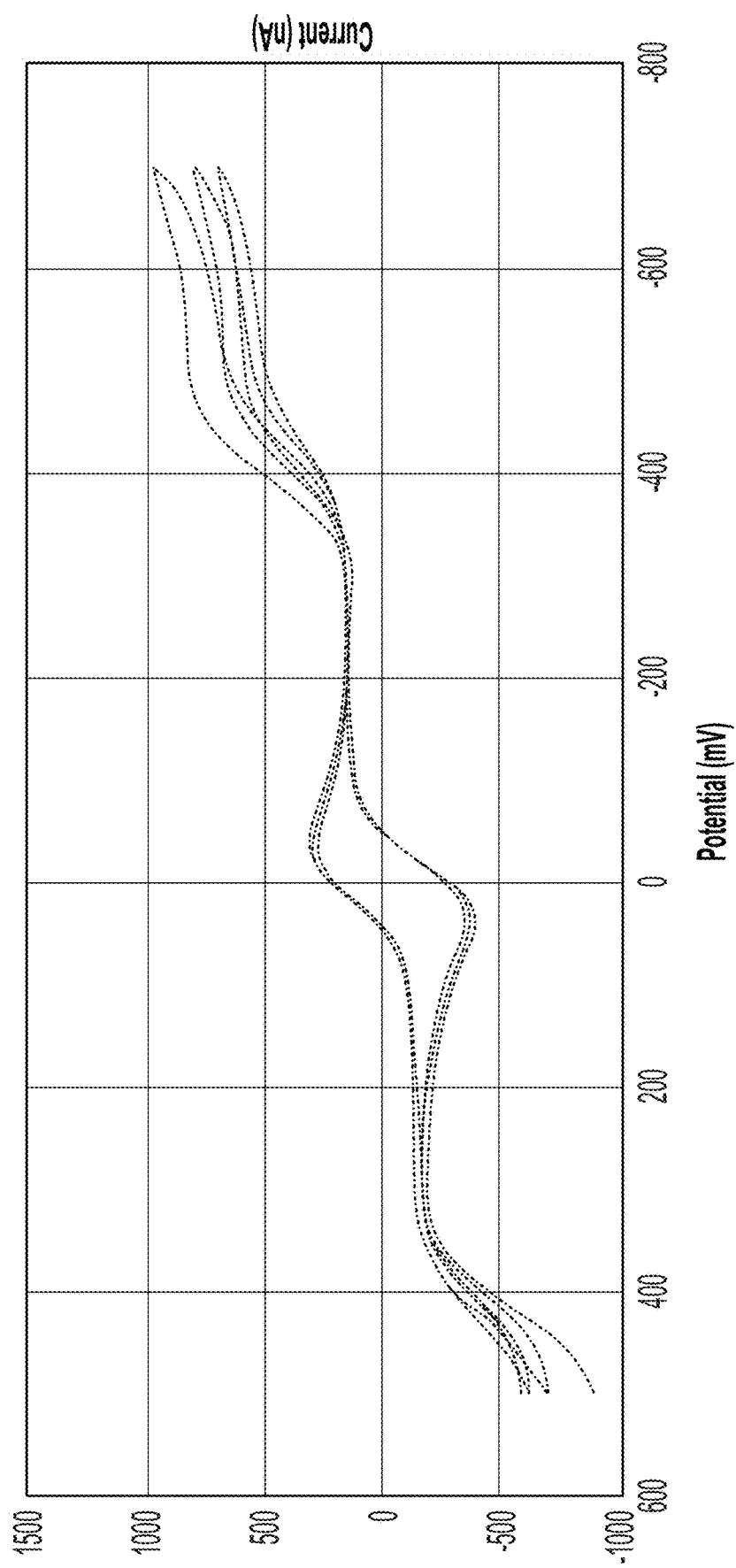
FIG. 4 shows testing results for an embodiment of an electrochemical test strip for use in determining hemoglobin A1C, total hemoglobin, and % HbA1C.

The reaction of ferrocyanide with the oxidized hemoglobin solution yielded a cyclic voltammogram of ferrocyanide in solution with and without blood/pre-analytical solution sample mixture shown in FIG. 4.

CONCLUSION

While specific embodiments have been described in the foregoing detailed description, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for the determination of A1C and total hemoglobin comprising:
   a sampler including a pre-analytical solution comprising components for lysing red blood cells, oxidizing free hemoglobin to $Fe^{+3}$, and cleaving FVH (fructosyl-valine-histidine) from free hemoglobin to form an electrochemical test solution;
   a first test strip including a reaction chemistry comprising fructosyl peptide oxidase and a reduced ruthenium mediator for electrochemical determination of A1C, configured to receive the electrochemical test solution; and
   a second test strip including a reaction chemistry comprising fructosyl peptide oxidase and ferrocyanide for electrochemical determination of total hemoglobin, configured to receive the electrochemical test solution.

2. The system of claim 1, wherein the pre-analytical solution includes a Neutral Enzyme Proteinase.

3. The system of claim 1, wherein the pre-analytical solution includes n-Tetradecyl-N,N-dimethyl-3-ammonio-1-propanesulfonate.

4. The system of claim 1, wherein the pre-analytical solution includes:
   t-Octylphenoxypolyethoxyethanol, Polyethylene glycol tert-octylphenyl ether
   880 mM Imidazole;
   10 mM NaCl;
   3 mM CaCl2;
   47.6 mM Tetradecyltrimethylammonium bromide (TTAB);
   8.1 mM 1,2-benzoisothiazol-3-one sodium salt; and
   35 kU/mL NEP (Neutral Enzyme Proteinase)-801.

5. The system of claim 1, wherein the pre-analytical solution is configured to be combined with a sample and applied to both the first and second test strip to achieve an analytical result.

* * * * *